United States Patent [19]

Miller et al.

[11] Patent Number: 5,683,640

[45] Date of Patent: Nov. 4, 1997

[54] METHOD OF MAKING DUAL LUMEN CATHETERS

[75] Inventors: John Miller; Victor Gamble, both of Salt Lake City, Utah

[73] Assignee: The Kendall Company, Mansfield, Mass.

[21] Appl. No.: 320,716

[22] Filed: Oct. 11, 1994

Related U.S. Application Data

[62] Division of Ser. No. 203,126, Feb. 28, 1994, Pat. No. 5,380,276.

[51] Int. Cl.$^6$ .............................. B29C 39/10; B29C 33/12
[52] U.S. Cl. ........................ 264/255; 264/263; 264/275
[58] Field of Search ................................. 264/263, 275, 264/277, 265, 271.1, 255

[56] References Cited

U.S. PATENT DOCUMENTS

| | | | |
|---|---|---|---|
| 3,959,429 | 5/1976 | Benning | 264/263 |
| 4,961,809 | 10/1990 | Martin | 264/322 |
| 5,135,599 | 8/1992 | Martin et al. | 264/322 |
| 5,169,568 | 12/1992 | Ainger, III | 264/263 |
| 5,302,336 | 4/1994 | Härtel et al. | 264/263 |
| 5,348,536 | 9/1994 | Young et al. | 264/171.27 |
| 5,356,587 | 10/1994 | Mitsui et al. | 264/263 |
| 5,409,652 | 4/1995 | Carter | 264/263 |

*Primary Examiner*—Angela Y. Ortiz
*Attorney, Agent, or Firm*—David J. Koris, Esq.

[57] ABSTRACT

A method of making a dual lumen catheter which is a unitary, elongated, flexible catheter tube that is substantially circular in cross-section. The catheter tube has an outer wall member forming a tube having a proximal end and a distal end portion adapted for insertion within a vein or artery of a patient. The outer wall member defines first and second coaxial lumens that are separated by an inner common support wall which is substantially circular and joins the outer wall. The first lumen extends longitudinally between the opposed distal and proximal ends of the catheter tube and terminates coextensive with the distal end portion of the catheter tube. The second lumen extends longitudinally from the proximal end of the catheter tube and terminates proximal to the distal end portion of the catheter tube. The second lumen is crescent-shaped in cross-section and substantially surrounds the first lumen. The cross-sectional areas of the first and second lumens are approximately equal. Each of the first and second lumens are totally smooth internally, thereby containing no ridges or connections which can promote formation of blood clots or cause hemolysis or damage to red blood cells during dialysis. The catheter tube is secured at its proximal end to the distal end of a hollow hub assembly.

5 Claims, 2 Drawing Sheets

METHOD OF MAKING DUAL LUMEN CATHETERS

This application is a division of application Ser. No. 08/203,126 filed Feb. 28, 1994 and now U.S. Pat. No. 5,380,276.

FIELD OF THE INVENTION

The invention relates in general to catheters, and more specifically to dual lumen catheters.

BACKGROUND OF THE INVENTION

Multilumen catheters are used to simultaneously infuse a plurality of fluids into a patient, the separate lumens of the catheters preventing fluids from mixing during the infusion process and before the fluids enter the patient's body. Preventing fluid mixing is particularly important where the simultaneously infused fluids are chemically incompatible.

Multilumen catheters are also useful for simultaneous infusion of fluids and withdrawal of samples of the patient's body fluids, thus avoiding the need for insertion of multiple separate catheters into the patient.

SUMMARY OF THE INVENTION

The invention features a dual lumen catheter comprising a unitary, elongated, flexible catheter tube that is substantially circular in cross-section, the tube having an outer wall member forming a tube having a proximal end and a distal end portion adapted for insertion within the vessel of a patient, the outer wall member defining first and second coaxial lumens that are separated by an inner common support wall which is substantially circular and joins the outer wall, the first lumen extending longitudinally between the opposed distal and proximal ends of the catheter tube and terminating coextensive with the distal end portion of the catheter tube, the second lumen extending longitudinally from the proximal end of the catheter tube and terminating proximal to the distal end portion of the catheter tube, the second lumen being crescent shaped in cross-section and substantially surrounding the first lumen, the cross-sectional areas of the first and second lumens preferably being substantially equal. As used herein, "substantially equal" means approximately or nearly identical, which will generally be within 90% of being identical.

Each of the lumens is totally smooth internally, thereby containing no ridges or connections which can promote formation of blood clots or cause hemolysis or damage to red blood cells, thereby inhibiting or materially reducing the likelihood of these occurrences during dialysis.

As heretofore noted, the catheter tube is secured at its proximal end to the distal end of a hollow hub assembly. The hub assembly is divided or splits at its proximal end into two hub segments each of which is connected to a tubing extension. The hub assembly and tubing extensions are unitary with the catheter tube with one of the tubing extensions being in fluid communication with the first lumen and the other tubing extension being in fluid communication with the second lumen.

In preferred embodiments, the dual lumen catheter further comprises a flexible collar extending around and from the proximal end of the catheter tube and terminating at or proximal to the distal end of the hub, the collar comprising a material that is more rigid than the catheter tube and thus offers support for the tube, providing a strain relief which serves to prevent kinking.

The dual lumen catheter further comprises at its distal end one or more port holes extending from the first or second lumen through the outer wall of the catheter tube; preferably, two side port holes enter into the circular first lumen and six side port holes enter into the crescent-shaped second lumen.

The dual lumen catheter may further comprise a releasable clamp fixed on each tubing extension.

Preferably, at least one of the lumens of the catheter is in fluid communication with a source of liquid to be introduced into the patient through the catheter. The dual lumen catheter, including the catheter tube and hub assembly, is preferably constructed of a semi-rigid material which is heat formable, e.g., polyurethane.

The invention also includes methods of kidney dialysis and plasmapheresis using the catheter of the invention.

In one method, the distal end of a catheter of the invention is implanted in a blood vessel, i.e., a vein or artery, such that the lumens of the catheter are in communication with fluid in the blood vessel so as to permit passage of fluid from the blood vessel through the lumen; fluid is then removed from the blood vessel via one lumen and treated to remove toxic metabolic waste; and the fluid is then re-infused into the blood vessel via the other lumen of the catheter.

According to another kidney dialysis method of the invention, a dialysis solution is infused into a patient's peritoneal cavity via the one lumen of a catheter of the invention, the dialysis solution is allowed to remain in the patient's peritoneal cavity for a time sufficient for blood impurities to be removed from the patient's blood by diffusion across the peritoneal membrane into the dialysis solution, and the dialysis solution is then drained from the peritoneal cavity via the other lumen of the catheter tube.

Catheters of the invention are particularly well-adapted for acute care kidney dialysis in that they comprise a unitary piece of flexible, i.e., semi-rigid, structurally stable material, such as a thermoplastic material, e.g., polyurethane. The internal surfaces of a catheter of the invention are completely smooth and have no nicks, crevices or joints upon which tissues in body fluids, particularly red blood cells, may accumulate and coagulate. This complete smoothness is attained by constructing the catheter tube and hub assembly, including hub joint and tube extensions which join to the dialysis tubing, by insert-molding or injection molding using heat but no solvents. Insert-molding into a unitary piece provides lumens which are totally smooth internally, i.e., contain no ridges, connections, etc., which can promote problems which are common in dialysis, e.g., formation of blood clots and cause hemolysis or damage to red blood cells. In addition, because catheters of the invention are unitary, there is a reduced risk of tip breakage upon insertion or removal of the catheter from the patient.

Other important advantages of catheters of the invention include greatly reduced susceptibility of the catheter tube to kinking and bending, thus greatly reducing risk to the patient of interrupting the dialysis process and potentially forming clots at the site of a kink. Catheter devices of the prior art which include a straight septum confer increased susceptibility to kinking in both directions. Some embodiments of the catheter of the invention include a strain-relieving collar which serves to further support the catheter tube and thus completely prevent bending of the tube during use.

The novel features as well as the nature and objects of the invention will be more fully understood from the following detailed description taken in conjunction with the accompanying illustrative drawings.

DETAILED DESCRIPTION OF THE INVENTION

EXAMPLE I

Figure 1:
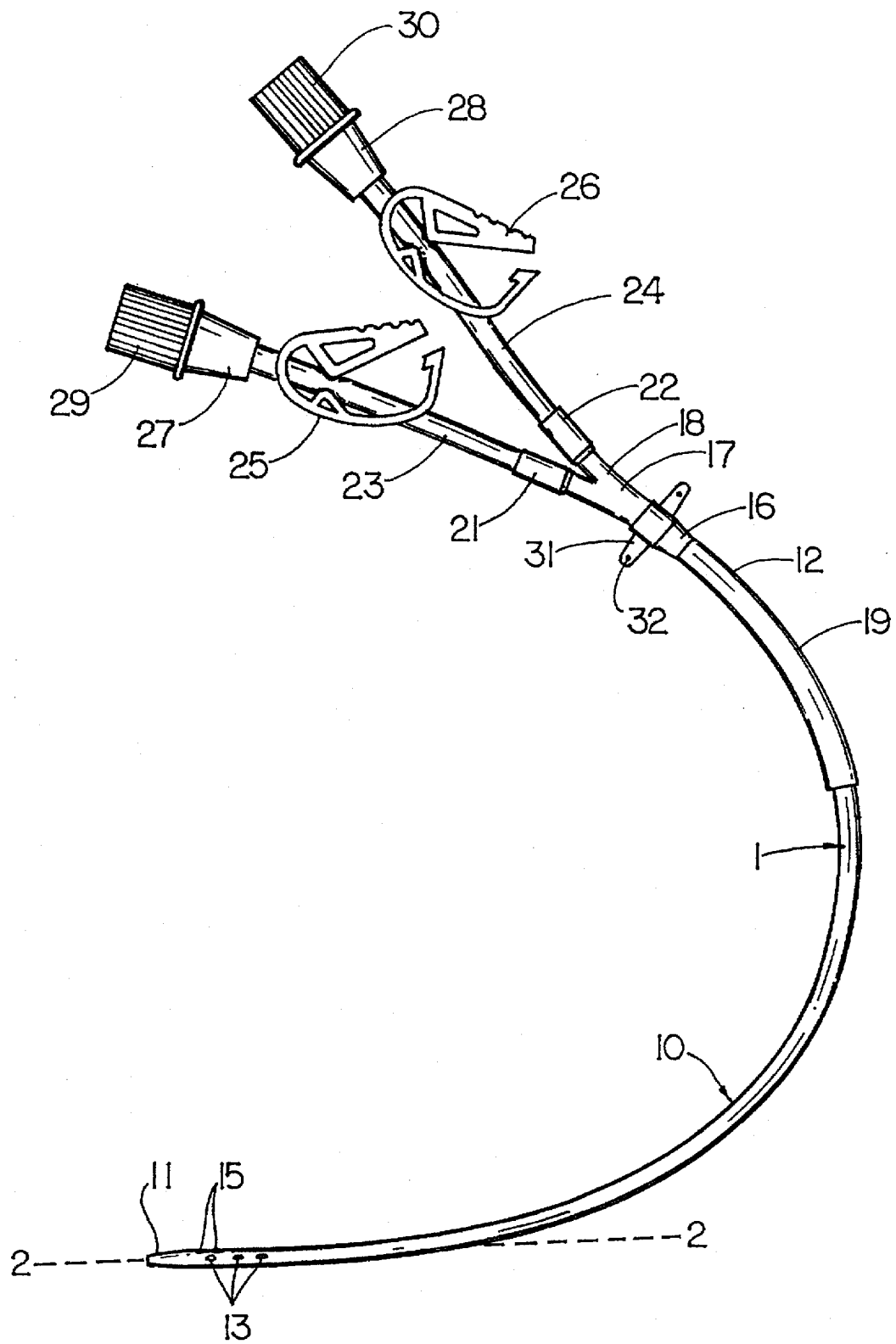
FIG. 1 is a schematic side view of the dual lumen catheter of the present invention.

Referring to FIG. 1, there is shown the preferred embodiment of the dual lumen catheter of this invention, generally designated as 1. The dual lumen catheter 1 has an elongated, flexible catheter tube 10 with a tapered distal end 11 capable of insertion into and being fed longitudinally within a blood vessel of a patient. Dual lumen catheter 1, including tube 10, hub assembly 17, and tube extensions 23,24, is made by insert molding or injection molding using a thermoplastic material, e.g., polyurethane. Thus, the catheter 1 is a unitary piece of flexible, i.e., semi-rigid, material which is completely smooth internally.

Those skilled in the art will appreciate that the tapered distal end 11 is conventionally introduced over a guide wire which has previously been placed within the blood vessel. Those skilled in the art will also understand that the common method to accomplish the placement of the guide wire within a blood vessel is the well-known "Seldinger Technique". After penetration by the needle, the catheter tube 10 is then fed longitudinally over the needle for a sufficient length so as to introduce within the blood vessel the lateral side ports 13, 15 opening to the interior of the catheter tube 10. The tube 10 is connected at its proximal end 12 to the distal end 16 of a fluid-conveying hollow hub assembly 17. Hub assembly 17 is divided or splits at its proximal end 18 into two integral hub segments 21,22 which are connected to tubing extensions 23,24 respectively. The tubing extensions 23,24 are in turn connected at their proximal ends to adapters 27,28 respectively for attachment to a suitable device or fluid source. As shown in FIG. 1, adapters 27,28 are provided with Luer lock caps 29,30 respectively, for covering the adapters when they are not in use connecting the tubing extensions. Also as shown in FIG. 1, conventional clamps 25,26 are provided to open and close tubing extensions 23,24 respectively, as desired.

In the preferred embodiment of the invention, catheter tube 10 is encased at its proximal end 12 by a collar 19 which serves to support tube 10, provides strain relief and further prevents bending during use. In addition, while not necessary to the practice of the invention, suture tab 31 having a pair of holes 32 is preferably provided for securing the catheter to the patient by means of a suture.

Figure 2:
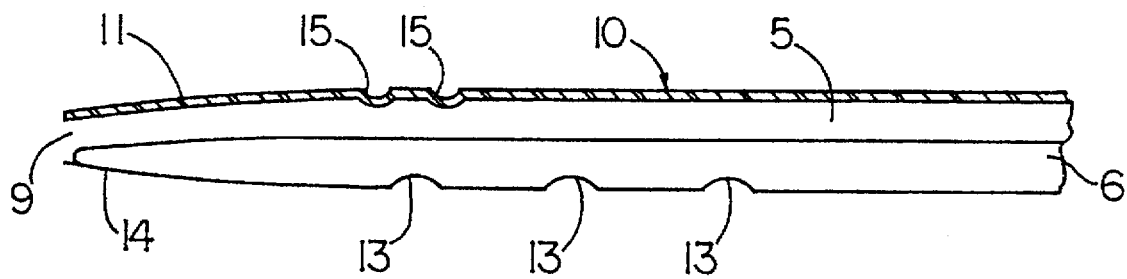
FIG. 2 is a side section view of the invention along Line 2–2' of FIG. 1.
Figure 3:
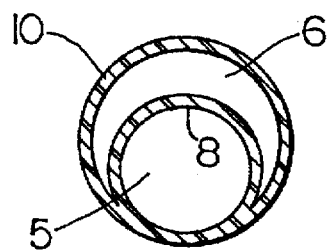
FIG. 3 is a cross-sectional view of the catheter tube of FIG. 1.
Figure 4:
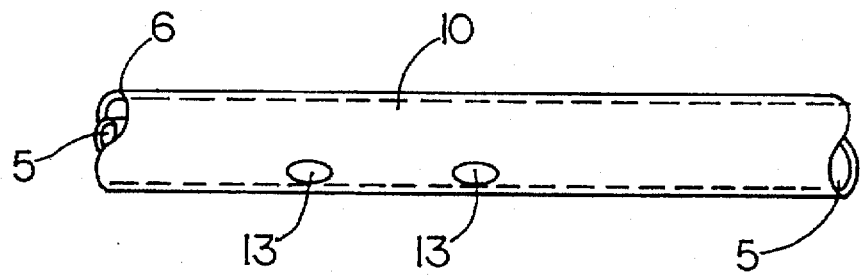
FIG. 4 is a bottom plan view of a portion of the catheter of FIG. 1, partially broken away.

Referring now to FIGS. 2–4, there is shown to be two longitudinally extending lumens 5,6 within the catheter tube 10. FIG. 3 shows the generally circular cross-section of the catheter tube 10 with the two lumens 5,6 contained therein and separated by septum 8. Lumen 5 is circular in cross-section, whereas lumen 6 is crescent-shaped in cross-section. Thus, the catheter contains two conduits corresponding to lumens 5 and 6. Circular lumen 5 will be most often used as a "venous" lumen, i.e., for returning clean blood to the patient, whereas crescent-shaped lumen 6 will be used as an "arterial" lumen, i.e., to remove blood from the patient via the side ports.

As seen, a novel feature of this invention is that the cross-sectional area of lumen 5 is substantially equal to the cross-sectional area of lumen 6, and thus lumens 5 and 6 are capable of holding a substantially similar volume of fluid. For purposes of the illustration, the catheter tubes may be of several sizes, e.g., 11, 10, or 8.5 french, corresponding to an outside diameter of on the order of 0.151 inch, 0.131 inch, or 0.114 inch, respectively. The circular lumen 5 will thus have an internal diameter of 0.079 inch in the size 11 french catheter tube. The size 11 french catheter will be useful primarily for insertion into an adult vessel for dialysis, the size 10 french catheter for insertion into a vessel of a smaller adult or a teenager, and the size 8.5 french catheter for insertion into a vessel of a child.

Catheter tube 10 terminates at distal end 11. Lumen 5 terminates through port 9 coextensive with the distal end 11, whereas lumen 6 terminates at portion 14 proximal to distal end 11.

Catheter tube 10 also includes side ports which allow for fluid communication between lumen 5 or lumen 6 and the external environment. Side ports 13 are separately spaced in the side wall of catheter tube 10. These lateral side ports 13 enable entry and discharge of fluid from lumen 6, as lumen 6 does not terminate in a port. Catheter 10 may also include side ports 15 which are spaced apart near the distal end 11 of the catheter and allow for fluid exchange between lumen 5 and the external environment. Fluids may be infused or blood withdrawn efficiently through lumen 5 through the end port 9 and side ports 15. In one embodiment of the invention, the distal end of catheter tube 10 will include two side ports 15 entering lumen 5, the circular lumen, and six side ports 13 entering lumen 6, the crescent-shaped lumen.

In accordance with the present invention, the dual lumens 5,6, are totally independent and non-communicative with one another so that fluid carried therein will not mix prior to entering the bloodstream.

The dual lumen catheter of the invention is constructed by insert molding as follows. Initially, the dual lumen tube is formed, e.g. by extrusion through a die. Side holes are then drilled through the outer wall at the distal end of the tube to reach the crescent or circular lumen. A mandrel is placed in the circular center lumen and the tip of the tube is heated so to allow the crescent-shaped lumen to collapse around the tip. Thus, the crescent lumen will terminate proximal to the distal end of the catheter tube. The thus-fabricated tube is then constructed as a unitary piece with the hub assembly as follows. Pins are inserted into the proximal ends of the crescent and circular lumens, the pins being shaped crescent and circular in cross-section, respectively. The proximal ends of the two pins diverge into a Y-shape to mimic the Y-shape of the hub assembly, as shown in FIG. 1. Extension tubing of a suitable size is inserted over the proximal end of each pin to within a short distance of the proximal end of the tube 10. The catheter tube and pins are then placed in a mold. A suitable polymeric material such as polyurethane of a somewhat stiffer nature after molding is then heated and injected into the mold to form the hub assembly as a unitary piece with the catheter tube and extension tubing. Upon cooling, the pins are removed, leaving channels which form the lumens, hub and extension tubing. Finally, a clamp is placed around each extension tube and luer fittings are solvent bonded at each extension tube end.

Depending on the source to which the tube extensions 23 and 24 are in communication, the dual lumen catheter of this invention may also be employed in per se known manner to continuously draw and return blood to a patient, monitor blood pressure and/or obtain a blood sample and/or infuse fluid into the blood vessel of the patient.

In use, a guidewire is first introduced into the desired blood vessel in the direction of the flow of blood, e.g. by the aforementioned "Seldinger Technique". Thereafter, the distal end 11 of the catheter tube 10 is fed into the puncture over the guide wire the desired distance until all the ports 13,15 are fully within the blood vessel. The luer-lock caps 29,30 are removed and the catheter tube 10 placed in fluid communication via extension tubings 23,24 with the desired device and/or fluid source for administration to the patient. As is well understood, when drug syringes are employed, for example, the drugs are injected into adapters 27,28 where they then flow through extension tubings 23,24 and then through hub assembly 17 into the dual lumens 5,6 respectively for introduction within the blood vessel through the distal portion of the catheter tube.

From the foregoing description it will thus be seen that the present invention provides a novel dual lumen catheter satisfying the objectives of the invention. The advantage of reduced kinking is solved by the curved nature of the septum 8, which renders the tube less susceptible to bending.

It will be appreciated that various changes may be made without departing from the scope of the invention herein contemplated. For example, while for purposes of illustration the invention has been described with reference to ports in each of the conduits 5,6, it is contemplated that a lesser or greater amount of ports may be utilized in each of the conduits, i.e. each may have but a single port or a plurality of ports greater than the two shown in the drawings.

EXAMPLE II

The methods and apparatuses of the invention are particularly useful in the treatment of patients experiencing renal disease, such as partial or total kidney failure. End stage renal disease currently affects over 100,000 patients in the United States, and over 400,000 patients worldwide. The patient load for this disease continues to grow at a seven percent annual rate.

Kidney failure may be acute or chronic. Acute failure may be caused by trauma, surgery, or disease but is time-limited as the patient heals. Chronic failure is permanent and will continue for the long term until the patient dies. Treatment for chronic or end stage renal disease consists of kidney transplant procedures or dialysis. Kidney transplant therapy is limited by the availability of suitable organ donors, and dialysis becomes the only remaining treatment (U.S. Pat. No. 5,151,082 Sep. 29, 1992 Gorsuch, et al.) for chronic kidney failure.

Dialysis is the process of removing metabolic waste products from the blood, a function performed by the natural kidney in a healthy condition. These waste products include salts, urea, creatinine, uric acid, and water. The substances are removed by diffusion across a membrane to a dialysate fluid which has a low concentration of the substances.

Dialysis takes place either by continuous ambulatory peritoneal dialysis in which the membrane used is the vascular membranes of the body in the peritoneal cavity, or hemodialysis in which an artificial membrane is used. In hemodialysis, blood is removed by placement of the catheter in an artery or vein, passed over one side of an extracorporeal porous dialyzer membrane, and returned to the body via the artery or vein into which the catheter is introduced. The membrane is made of cellulose or another suitable material. Dialysis fluid is passed over the other side of the dialyzer membrane and the metabolic waste products pass through the porous membrane from the blood to the dialysate by the process of diffusion. The pores in the membrane are sized such that the waste products pass through the membrane but other blood components such as hemoglobin, albumin, gamma globulin, virus and bacterial bodies, are too large and cannot pass through the pores. Excess water is passed through the membrane by an ultrafiltration process (U.S. Pat. No. 5,151,082 Sep. 29, 1992 Gorsuch et al.) in which a positive pressure gradient is created between the blood and the dialysate on opposite sides of the membrane.

Although hemodialysis is widely used as a treatment for kidney failure, there are significant problems associated with the procedure. For example, the removal of whole blood from the body, followed by processing and returning that blood, causes clotting, infection, and damage to the cells, as well as damage to proteins and other blood components. Therefore, it is important that the catheter apparatus used in the procedure be as efficient as possible in removing blood from and reinfusing cleansed blood to the patient, such that the flow of fluids out of and back into the patient is as continuous as possible and minimizes the opportunity for infection, clotting, and tissue trauma.

Another treatment of renal disease is through a procedure known as intermittent peritoneal dialysis. In this procedure, a dialysis solution is infused into the patient's peritoneal cavity by means of tubing and a catheter. The peritoneum, which defines a peritoneal cavity, contains many small blood vessels and capillary beds which act as a natural semipermeable membrane. The natural membrane may be contrasted with the artificial membrane used in hemodialysis. In both cases, however, impurities and toxins in the blood are removed by diffusion across a membrane such as a cellulose membrane of the artificial kidney or a peritoneal natural membrane of the peritoneal cavity. Dialysis solutions remain in the patient's peritoneal cavity in intermittent peritoneal dialysis for a time sufficient for blood impurities to be removed by diffusion across the peritoneal membrane into the dialysis solution. The impurity containing dialysis solution then is drained from the peritoneal cavity by means of a catheter and tubing and a fresh supply of dialysis solution is infused. Again, it is important that the catheter be adapted so as to efficiently and continuously infuse and remove fluids to and from the patient with a minimum of trauma.

Thus, in use in kidney dialysis, the dual lumen catheter of the invention 10 is inserted at end 11 into the subclavian artery, femoral vein, or jugular vein of the patient such that ports 13,15 are contained within the vein and thus are in fluid communication with the vein or artery. Luer lock caps 29,30 are removed from adapters 27,28, respectively, and connected to the dialysis machine via tubing extensions (not shown). When dialysis is commenced, clamps 25,26 are released to allow flow of fluid through tubing extensions 23,24. The dual lumen catheter of the invention is particularly useful for kidney dialysis in that it is flexible along its length by virtue of the curved septum 8. Thus, the catheter tube will not kink or buckle during use, and will not expose the patient to such risks as damage to red blood cells potentially resulting in formation of blood clots in the reinfused blood. During dialysis, venous blood is removed from the patient via lumen 6 and cleansed and returned to the patient via lumen 5. The catheter of the invention, because it is a unitary piece of semi-rigid, structurally stable material, is completely smooth internally in both lumens, thus further reducing the risk damage to red blood cells and clotting. In addition, because of its unitary construction, there is little danger of that the distal tip of the tube will break off during insertion into or removal from the patient.

Alternatively, catheters of the invention may be used for another method of dialysis described above, i.e., peritoneal dialysis. According to this method of the invention, a dialysis solution is infused into a patient's peritoneal cavity via lumen 5 of the catheter tube described herein, the dialysis solution is allowed to remain in the patient's peritoneal cavity for a time sufficient for blood impurities to be removed from the patient's blood by diffusion across the peritoneal membrane into the dialysis solution, and the dialysis solution is then removed from the patient's peritoneal cavity via the lumen 6 of the catheter tube. For either of the above methods, the invention is not limited to fluid infusion or removal via lumens 5 and 6 respectively, but may also be performed using lumen 5 for fluid removal and lumen 6 for fluid infusion.

Accordingly, it is to be understood that the foregoing description and accompanying drawings are merely illustrative of the preferred embodiment of the dual lumen catheter of the present invention, and that no limitations are intended other than as defined in the appended claims.

We claim:

1. A method for making a unitary dual lumen catheter and hub, comprising:

(a) providing a dual lumen catheter comprising:

a unitary, elongated, flexible catheter tube that is substantially circular in cross-section, said tube having an outer wall member forming a tube having a proximal end and a distal end portion adapted for insertion within the vein of a patient, the outer wall member defining first and second lumens that are separated by an inner common support wall which is substantially circular and joins said outer wall, said first lumen extending longitudinally between the opposed distal and proximal ends of the catheter tube and terminating coextensive with said distal end portion of said catheter tube, said second lumen extending longitudinally from the proximal end of the catheter tube and terminating proximal to said distal end portion of said catheter tube, said second lumen further comprising adjacent said distal end a port hole extending through said outer wall, said second lumen being crescent shaped in cross-section and substantially surrounding said first lumen, the cross-sectional areas of the first and second lumens being approximately equal, each of said first and second lumens being totally smooth internally, thereby containing no ridges or connections which can promote formation of blood clots or cause hemolysis or damage to red blood cells during dialysis;

(b) inserting within said proximal tube end a support shaped to fit within said first and second lumens, said support extending from said tube proximal end in a branched configuration;

(c) placing said dual lumen catheter with inserted support of step (b) into an insert mold shaped to hold said catheter at said catheter distal end and to hold a softened material around said branched configuration at said catheter proximal end;

(d) placing a softened material in said insert mold around said branched configuration and allowing said material to harden to form a branched hub integral with said catheter proximal end; and (e) removing said support.

2. The method of claim 1, further comprising the step, prior to said step (d), of placing extension tubing over the extended branched configuration of said support such that, upon performing said step (d), said branched hub is integral with said catheter proximal end at one end and said extension tubing at the other end.

3. The method of claim 2, wherein said support comprises a pin which is branched at its proximal and distal ends, the distal end branch being shaped crescent and circular in cross-section so as to slide within said dual lumen catheter tube, the proximal end branch being Y-shaped.

4. The method of making a unitary dual lumen catheter having a hub comprising the steps of:

(a) initially forming a dual lumen catheter having a unitary, elongated flexible tube that is substantially circular in cross-section, the tube having an outer wall member forming a tube having a proximal end and an opposed distal end portion adapted for insertion within the vein of a patient, the outer wall member defining first and second lumens that are separated by an inner common support wall which is substantially circular and joins the outer wall, the first lumen extending longitudinally between the opposed distal and proximal ends of the catheter tube and terminating coextensive the distal end portion of the catheter tube, the second lumen extending longitudinally from the proximal end of the catheter tube and terminating proximal to the distal end portion of the catheter tube, said second lumen further comprising adjacent said distal end a port hole extending through said outer wall member, the first lumen being circular in cross-section and the second lumen being crescent-shaped in cross-section and substantially surrounding the first lumen, the cross-sectional areas of the first and second lumens being approximately equal;

(b) inserting within the proximal end of the first lumen a first support pin shaped to fit within the first lumen and inserting within the proximal end of the second lumen a second support pin shaped to fit within the second lumen, the pins extending from the proximal end of the tube in a branched configuration;

(c) placing an extension tube over each of the support pins of the branched configuration, each extension tube being inserted a short distance within the proximal end of the lumen from which the underlying support pin extends;

(d) placing the dual lumen catheter with the extension tubes and inserted support pins into an insert mold shaped to hold the catheter at the catheter distal end and to hold a softened material around a distal portion of the branched configuration of the extension tubes and pin supports extending from the catheter proximal end;

(e) placing the softened material in the insert mold around the branched configuration;

(f) allowing the softened material to harden to form a branched hub integral with the catheter proximal end; and (g) thereafter removing the support pins from within the catheter and the extension tubes, thereby leaving channels which form the lumens, hub and extension tubes.

5. The method as defined in claim 4 including the step of fastening a luer fitting on the end of each of the extension tubes after removal of the support pins.

* * * * *